United States Patent [19]
Adams, Jr.

[11] 4,328,228
[45] May 4, 1982

[54] 2,3-DIHALO-6-QUINOXALINESULFONYL FLUORIDES

[75] Inventor: John B. Adams, Jr., Hockessin, Del.

[73] Assignee: E. I. Du Pont de Nemours and Company, Wilmington, Del.

[21] Appl. No.: 167,431

[22] Filed: Jul. 8, 1980

[51] Int. Cl.$^3$ .................... C07D 241/44; A01N 43/60
[52] U.S. Cl. .................................. 424/250; 544/356; 71/92
[58] Field of Search ........................ 544/356; 424/250

[56] References Cited

U.S. PATENT DOCUMENTS 4,096,152  6/1978  Möller et al. ........................ 544/356
4,258,044  3/1981  Woods ................................ 544/356

FOREIGN PATENT DOCUMENTS

39/27255  11/1964  Japan ................................... 544/356
1043042   9/1966  United Kingdom ................ 544/356
1072008   6/1967  United Kingdom .

OTHER PUBLICATIONS

Sutter et al, "Organic Chemistry of Sulphur", 1948, p. 455.

Primary Examiner—Mark L. Berch

[57] ABSTRACT

2,3-Dihalo-6-quinoxalinesulfonyl fluoride compounds are useful as fungicides and insecticides.

21 Claims, No Drawings

2,3-DIHALO-6-QUINOXALINESULFONYL FLUORIDES

BACKGROUND OF THE INVENTION

This invention relates to compounds having useful agricultural properties. In particular, this invention relates to 2,3-dihalo-6-quinoxalinesulfonyl fluoride compounds.

Japanese patent application Publication No. 39-27257 issued on Nov. 28, 1964 discloses compounds having the formula

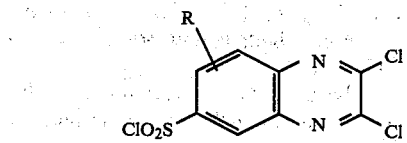

wherein R is hydrogen, nitro, halogen, lower alkyl or lower alkoxy. The publication also discloses a process for preparing these compounds which are stated to be useful as intermediates for making dyes, drugs and agricultural chemicals.

Japanese patent application Publication No. 40-23196 issued on Oct. 13, 1965 discloses agricultural fungicides having as an effective component one or more of the compounds represented by the following general formula:

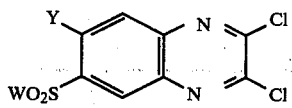

where Y is H and W is SR with R representing a lower alkyl group. The disclosed compounds are stated to be particularly useful against certain rice crop diseases. Japanese patent application Publication No. 39-27255 issued on Nov. 28, 1964 discloses compounds of formula III wherein W is OR, with R representing a lower alkyl group, and Y is hydrogen, halogen, lower alkyl or lower alkoxy. The compounds are disclosed to be useful as agricultural chemicals, drugs, and the like, and as intermediates. Belgian Pat. No. 635,579 issued on Nov. 14, 1963 discloses compounds of formula III wherein Y is hydrogen and W is a $NR_1R_2$ group with $R_1$ and $R_2$ being hydrogen, aryl, or cyclohexyl, or $NR_1R_2$ taken together are morpholino or piperidino. The compounds are disclosed to be useful as fungicides.

Canadian Pat. No. 713,562 discloses compounds of general formula IV wherein X is Cl or Br; W is SCX'Y'R' with X' and Y' being oxygen or sulfur and R' being substituted alkyl, aralkyl, cycloalkyl, or aryl; Y is a group inert to acid halides; and n is 0-4. Acaricidal and fungicidal utility is disclosed for the compounds.

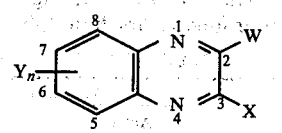

Japanese patent application Publication No. 12317/65 discloses compounds of formula IV wherein W is AB with A being oxygen or sulfur and B being lower alkyl, alkenyl, hydroxyalkyl, or optionally substituted phenyl or benzyl; X is the same as W or is Cl; n is 1; and Y is 6-$NO_2$. The compounds are disclosed as having useful fungicidal activity. German Pat. No. 1,194,631 discloses compounds of formula III wherein X, Y and W are Cl and n is 0-4; said compounds being useful as fungicides.

The rapidly increasing population of the world creates a strong demand for new agents to protect crops from pests.

SUMMARY OF THE INVENTION

There are disclosed compounds of the formula

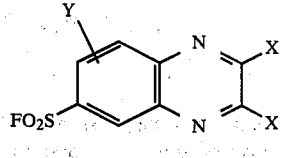

wherein
X is F or Cl;
Y is H, Cl, Br, $CH_3O$, $NO_2$ or $CH_3$.

There are also disclosed agricultural compositions containing a compound of formula I and methods of using these compounds as fungicides and insecticides.

DETAILED DESCRIPTION OF THE INVENTION

The compounds of the invention are 2,3-dihalo-6-quinoxalinesulfonyl fluoride compounds of the formula

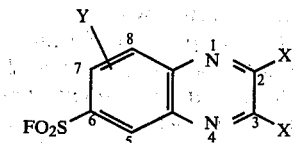

wherein
X is F or Cl;
Y is H, Cl, Br, $CH_3O$, $NO_2$ or $CH_3$.

Compounds of the invention which are preferred because of their higher activity and/or lower cost are those wherein X is Cl.

More preferred for the same reasons are compounds which, in addition to having X equal to Cl, have Y in the 7-position, i.e., Y is a 7-substituent.

Most preferred for the same reasons are compounds of the more preferred scope wherein Y is H, Cl or $CH_3$.

Specifically preferred for reasons of highest biological activity and/or lowest cost is the compound 2,3,7-trichloro-6-quinoxalinesulfonyl fluoride.

The compounds of the invention provide effective control of a great variety of pests. Application of the compounds of the invention by the methods disclosed herein entirely precludes or reduces damage to plants and organic materials, due to fungi and insects. In addition, the compounds of the invention prevent insect populations from expanding or reduce them to a low level or even eliminate insect populations.

SYNTHESIS

As shown by the equation below, the compounds of the invention can be prepared by a process in which aqueous fluoride is reacted with the sulfonyl chloride (formula V) of the compound corresponding to the compound of formula I.

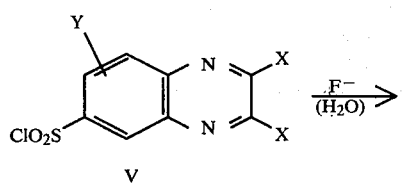

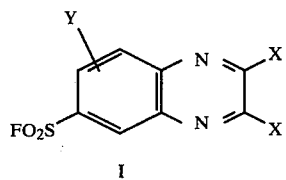

To effect the reaction a suspension of the sulfonyl chloride in aqueous sodium or potassium fluoride is heated, e.g., at 90°–130° C. for ¼ to 1 hour, the higher temperatures requiring the shorter reaction times. Optionally, there can also be present a watermiscible cosolvent, such as dioxane, tetrahydrofuran, acetonitrile, or ethylene glycol dimethyl ether. This method for conversion of sulfonyl chlorides to sulfonyl fluorides is discussed in J. Org. Chem. 28, 3426 (1963).

Sulfonyl chlorides can also be readily converted to sulfonyl fluorides at lower temperatures in the presence of a phase-transfer catalyst. In such a conversion a solution of the sulfonyl chloride in a water-immiscible solvent, such as methylene chloride, ethyl acetate, diethyl ether, or toluene, is stirred with aqueous sodium or potassium fluoride in the presence of a catalytic amount of a phase-transfer catalyst, e.g., benzyltriethylammonium chloride or tetrabutylammonium bromide, until the reaction is substantially complete. Reaction temperatures can range from about −10° to 80° C. and reaction times can be from about ¼ to 24 hours or longer if desired. This conversion method is discussed in U.S. Pat. No. 4,060,549.

Additional literature references for conversion of sulfonyl chlorides to sulfonyl fluorides include:
 "The Organic Chemistry of Sulfur", C. M. Suter, John Wiley & Sons, 1948, p. 453–458; and
 J. Am. Chem. Soc., 83, 4038 (1961)

The starting sulfonyl chlorides of formula V are prepared by suitable modification of the method disclosed in Japanese patent application Publication No. 39-27,257.

The invention is further illustrated by the following examples in which all temperatures are degrees C. and all percentages are by weight unless otherwise stated.

EXAMPLE 1

2,3,7-Trichloro-6-quinoxalinesulfonyl Fluoride

A mixture of 2.00 g of 2,3,7-trichloro-6-quinoxalinesulfonyl chloride, 4 g of sodium fluoride and 16 ml of water was stirred and boiled under reflux for one hour. The reaction mixture was cooled and filtered to obtain a tan solid which was recrystallized from aqueous acetone and then from hexane to provide 1.2 g. of 2,3,7-trichloro-6-quinoxalinesulfonyl fluoride as a yellow solid having melting point of 109°–111°. Mass spectral analysis shows a molecular ion with m/e of 314 which corresponds to the molecular weight for 2,3,7-trichloro-6-quinoxalinesulfonyl fluoride.

EXAMPLE 2

2,3,7-Trichloro-6-quinoxalinesulfonyl Fluoride

To a solution of 46 g of 2,3,7-trichloro-6-quinoxalinesulfonyl chloride in 200 ml of methylene chloride were added 0.42 g of benzyltriethylammonium bromide and a solution of 20.2 g of potassium fluoride in 20.9 ml of water. The resulting mixture was stirred for 17.5 hours at ambient temperature, filtered, dried over magnesium sulfate, treated with activated carbon and filtered again. Solvent was removed under vacuum, leaving a yellowish solid which was recrystallized from hexane to provide 35 g of 2,3,7-trichloro-6-quinoxalinesulfonyl fluoride as a light-yellow solid, having a melting point of 111°–113°.

Elemental Analyses (%): Calculated for $C_8H_2Cl_3FN_2O_2S$: C, 30.4; N, 8.9; S, 10.2; Found: C, 30.2; N, 8.8; S, 10.4.

By procedures similar to those set forth in Examples 1 and 2 with the appropriate sulfonyl chloride starting material, the compounds listed in Table 1 can be prepared.

TABLE 1

2,3-Dihalo-6-quinoxalinesulfonyl Fluorides

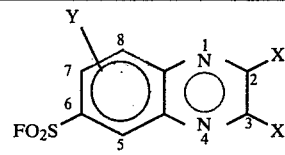

| X | Y |
|---|---|
| Cl | 7-Br |
| Cl | 5-Cl |
| Cl | 8-Cl |
| Cl | 7-OCH$_3$ |
| Cl | 7-NO$_2$ |
| Cl | 7-CH$_3$ |
| Cl | H |
| F | 7-Cl |

Formulations

Useful formulations of the compounds of formula I can be prepared in conventional ways. They include dusts, suspensions, dispersible solids such as wettable powders and dispersible granules, and the like. Many of them can be applied directly. Sprayable formulations can be extended in suitable media and used at spray volumes of from a few liters to several hundred liters per hectare. High-strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table 2.

TABLE 2

| | Weight Percent* | | |
|---|---|---|---|
| | Active Ingredient | Diluent(s) | Surfactant(s) |
| Dispersible Solids | 20–90 | 0–74 | 1–10 |
| Oil Suspension, Solutions, Emulsifiable Concentrates | 5–50 | 40–95 | 0–15 |
| Dusts | 1–25 | 70–99 | 0–5 |
| High-Strength Compo- | | | |

TABLE 2-continued

| | Weight Percent* | | |
|---|---|---|---|
| | Active Ingredient | Diluent(s) | Surfactant(s) |
| sitions | 90–99 | 0–10 | 0–2 |

*Active Ingredient plus at least one of a Surfactant or a Diluent equals 100 weight percent.

Lower or high levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, New Jersey, but other solids, either mined or manufactured, can be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084).

For further information regarding the art of formulation, see for example:
R. R. Shaffer, U.S. Pat. No. 3,560,616 Feb. 2, 1971, Col. 3 Line 48 through Col. 7 Line 26 and Examples 3–9, 11–18.
E. Somers, "Formulation", Chapter 6 in Torgeson, "Fungicides", Vol. I, Academic Press, New York, 1967.

EXAMPLE 3

| Wettable Powder | |
|---|---|
| 2,3,7-trichloro-6-quinoxaline-sulfonyl fluoride | 50% |
| sodium alkylnaphthalenesulfonate | 3% |
| sodium N-methyl-N-oleoyltaurate | 2% |
| diatomaceous earth | 45% |

The ingredients can be blended, coarsely hammer-milled and then air milled to produce particles of active essentially all below 10 microns in diameter. The product can be reblended before packaging. All other compounds of the invention can be formulated in a similar manner.

EXAMPLE 4

| Oil Dispersible Powder | |
|---|---|
| 2,3,7-trichloro-6-quinoxaline-sulfonyl fluoride | 40% |
| sodium dodecylbenzenesulfonate | 3% |
| polyvinyl pyrrolidone | 1% |
| amorphous silica | 1% |
| starch | 55% |

The ingredients can be thoroughly blended, passed through an air mill to produce an average particle size under 15 microns, reblended, and sifted through a U.S.S. No. 50 sieve (0.3 mm opening) before packaging.

This formulation can be dispersed into an aliphatic oil prior to spraying on crops.

EXAMPLE 5

| Dust | |
|---|---|
| 2,3,7-trichloro-6-quinoxalinesulfonyl fluoride | 10% |
| attapulgite | 10% |
| pyrophyllite | 80% |

The active ingredient can be blended with attapulgite and then passed through a hammer mill to produce particles substantially all below 200 microns in diameter. This ground concentrate can be then blended with powdered pyrophyllite until homogeneous.

EXAMPLE 6

| High-Strength Concentrate | |
|---|---|
| 2,3,7-trichloro-6-quinoxalinesulfonyl fluoride | 98.5% |
| silica aerogel | 0.5% |
| synthetic amorphous fine silica | 1.0% |

The ingredients can be blended and ground in a hammer mill to produce a high strength concentrate practically all passing a U.S.S. No. 50 sieve (0.3 mm openings). This material may then be formulated in a variety of ways.

EXAMPLE 7

| Emulsifiable Concentrate | |
|---|---|
| 2,3,7-trichloro-6-quinoxalinesulfonyl fluoride | 35.0% |
| blend of polyoxyethylene ethers | 5.0% |
| xylenes | 60.0% |

The ingredients can be combined and stirred to produce an emulsifiable concentrate.

Utility

Fungicide

The compounds of this invention are effective for the control of a broad spectrum of plant diseases on a variety of host plants with a margin of plant safety. The diseases are incited by fungal pathogens represented by, but not limited to, *Venturia inaequalis, Piricularia oryzae, Phytophthora infestans, Uromyces phaseoli,* and *Puccinia graminis.*

Disease control is accomplished by applying the compounds of this invention to the portion of the plant to be protected. The compounds are applied as a preventive treatment prior to inoculation with the pathogen or after inoculation as a curative, post-infection treatment.

Rates of application for compounds of this invention will be influenced by specific host plants, fungal pathogens, and many factors of the environment and must be determined under use conditions. Foliage sprayed with concentrations ranging from about 1 to 500 ppm active ingredient can be protected from disease under suitable conditions. Compositions of this invention may contain, in addition to compounds of this invention, conventional pesticides, such as insecticides, miticides, bactericides, nemacticides, acaricides, fungicides, or other agricultural chemicals such as growth modifying agents and fertilizer ingredients, and the like. The proper choice of conventional pesticide and their amounts can be made by one skilled in the art of protecting plants from pest depredation.

The following are illustrative of other fungicides that may be included in compositions or added to sprays containing one or more of the active compounds of this invention:

bis(dimethylthiocarbamoyl)disulfide; or tetramethylthiuram disulfide (thiram);
metal salts of ethylenebisdithiocarbamic acid or propylenebisdithiocarbamic acids, e.g. manganese, zinc, iron and sodium salts (maneb or zineb);
n-dodecylguanidine acetate (dodine);
N-(trichloromethylthio)phthalimide (folpet);
N-[(trichloromethyl)thio]-4-cyclohexene-1,2-dicarboximide (captan);
cis-N-[(1,1,2,2,-tetrachloroethyl)thio]-4-cyclohexene-1,2-dicarboximide (captafol);
2,4-dichloro-6-(o-chloroanilino)-α-triazine ("Dyrene");
3,3'-ethylenebis(tetrahydro-4,6-dimethyl-2H-1,3,5-thiadiazine-2-thione) (milneb);
triphenyltin hydroxide (fentin hydroxide);
triphenyltin acetate (fentin acetate);
N'-dichlorofluoromethylthio-N,N-dimethyl-N'-phenylsulfamide (dichlorofluanid);
tetrachloroisophthalonitrile (chlorothalonil);
tribasic copper sulfate;
fixed copper;
sulfur;
methyl 1-(butylcarbamoyl)-2-benzimidazolecarbamate (benomyl);
methyl 2-benzimidazolecarbamate (carbendazim);
1,2-bis(3-methoxycarbonyl-2-thioureido)benzene (methyl thiophanate);
2-cyano-N-(ethylcarbamoyl)-2-methoxyiminoacetamide;

The agricultural chemicals listed above are merely exemplary of compounds that may be mixed with the active compounds of the invention to broaden the spectrum of disease control.

In the following examples, which more clearly illustrate the biological activity of the compounds of this invention, percent disease control was calculated by the formula $$100 - \left[ \frac{\text{disease rating on treated}}{\text{disease rating on untreated}} \times 100 \right] = \text{percent control}$$

No plant injury was noted when host plants specified in the following examples were treated with compounds of this invention at the specified application rates.

EXAMPLE 8

A compound of the invention is dissolved in acetone in an amount equal to 10% of the final volume and then suspended at a concentration of 16 ppm in purified water containing 250 ppm of Trem ® 014 surfactant which consists of nonionic polyhydric alcohol esters and is manufactured by Nopco Chemical Division of Diamond Shamrock. This suspension is sprayed to the point of runoff on seedling apple plants. The following day, the plants are inoculated with a spore suspension of the fungus *Venturia inaequalis* and incubated in a saturated humidity chamber at 20° for 24 hours, and then in a greenhouse for an additional 11 days before disease ratings are made. As shown in the following table, the compound of the invention provides excellent disease control, as treated plants have no foliar lesions in contrast to untreated plants which are covered with scab lesions.

| Compound | Percent Control apple scab |
|---|---|
| 2,3,7-trichloro-6-quinoxaline-sulfonyl fluoride | 100 |

EXAMPLE 9

A compound of the invention is dissolved in acetone in an amount equal to 10% of the final volume and then suspended at a concentration of 80 ppm in purified water containing 250 ppm of Trem ® 014 surfactant. This suspension is sprayed to the point of run-off on rice seedlings. The following day, the rice seedlings are inoculated with a spore suspension of the fungus *Piricularia oryzae* and incubated in a saturated humidity chamber at 23° C. for 24 hours, and then in a greenhouse for an additional 7 days before disease ratings are made. As shown in the following table, the compound of this invention provides excellent disease control, as treated plants have only a few foliar lesions in contrast to untreated plants which have numerous blast lesions on each leaf.

| Compound | Percent Control Rice Blast |
|---|---|
| 2,3,7-trichloro-6-quinoxaline-sulfonyl fluoride | 95 |

EXAMPLE 10

A compound of the invention is dissolved in acetone in an amount equal to 10% of the final volume and then suspended at a concentration of 100 ppm in purified water containing 250 ppm of Trem ® 014 surfactant. This suspension is sprayed to the point of run-off on seedling tomato plants. The following day the plants are inoculated with a spore suspension of *Phytophthora infestans* and incubated in a saturated humidity chamber at 20° for 24 hours and then in a growth room for an additional 4 days before disease ratings are made. As shown in the following table, the compound of this invention provides excellent disease control as treated plants have no foliar lesions to untreated plants which are covered with late blight lesions.

| Compound | Percent Control Tomato Late Blight |
|---|---|
| 2,3,7-trichloro-6-quinoxalinesulfonyl fluoride | 100 |

EXAMPLE 11

A compound of the invention is dissolved in acetone in an amount equal to 10% of the final volume and then suspended at a concentration of 80 ppm in purified water containing Trem® 014 surfactant. This suspension is sprayed to the point of run-off on Pinto bean seedlings. The following day, the plants are inoculated with a spore suspension of the fungus *Uromyces phaseoli var. typica* and incubated in a saturated humidity chamber at 20° for 24 hours, and then in a greenhouse for an additional 7 days before disease ratings are made. As shown in the following table, the compound of this invention provides excellent disease control, as treated plants have only a few rust pustules in contrast to untreated plants which had numerous rust pustules on each leaf.

| Compound | Percent Control Bean Rust |
|---|---|
| 2,3,7-trichloro-6-quinoxaline-sulfonyl fluoride | 94 |

EXAMPLE 12

A compound of the invention is dissolved in acetone in an amount equal to 10% of the final volume and then suspended at a concentration of 80 ppm in purified water containing 250 ppm of Trem® 014 surfactant. This suspension is sprayed to the point of run-off on wheat seedlings. The following day, the plants are inoculated with a spore suspension of *Puccinia graminis var. tritici* and incubated in a saturated humidity chamber at 20° for 24 hours and then in a greenhouse for an additional 7 days before disease ratings are made. As shown in the following table, the compound of this invention provides excellent disease control, as treated plants have no rust pustules in contrast to untreated plants which have numerous rust pustules on each leaf.

| Compound | Percent Control Wheat Rust |
|---|---|
| 2,3,7-trichloro-6-quinoxaline-sulfonyl fluoride | 100 |

Insect Control

The compounds of this invention are useful for control of arthropods detrimental to agriculture and public health. They control anthropod pests belonging to the orders Acari, Coleoptera, Diptera, Lepidoptera. More specifically, arthropods controlled by compounds of this invention include but are not limited to: two-spotted mite (*Tetranychus urticae*), boll weevil (*Anthonomus grandis*), housefly (*Musca domestica*) and beet armyworm (*Spodoptera exigua*).

The arthropods are controlled by applying material in a convenient formulation to the locus of infestation, to the area to be protected or to the pests themselves. For control of arthropods in agricultural crops, the compound is generally applied to foliage or other plant parts which are infested or which are to be protected. For control of non-agricultural pests, the compound is generally applied to resting or breeding sites, or to the insect directly. Effective amounts to be applied depend on the species to be controlled, its life stage, its size and location, the amount of rainfall, moisture, temperature, type of application and other variables. Application at a rate of ⅛-20 kilograms/hectare can provide control under suitable conditions.

As mentioned earlier, the compound of this invention can be mixed with other biologically active compounds in order to achieve desired results with a minimum expenditure of time, effort and material. Amounts of other biologically active materials added for each part by weight of the compound of this invention can vary from 0.0625 to 25 parts by weight. Suitable agents of this type are well known to those skilled in the art. In addition to those previously listed, others are listed below:

Bactericides streptomycin sulfate

Acaricides senecioic acid, ester with 2-sec-butyl-4,6-dinitrophenol ("Morocide")
6-methyl-1,3-dithiolo[2,3-b]quinoxolin-2-one ("Morestan")
ethyl 4,4'-dichlorobenzilate (Chlorobenzilate®)
1,1-bis(p-chlorophenyl)-2,2,2-trichloroethanol (Kelthane®)
bis(pentachloro-2,4-cyclopentadienyl) (Pentac®)
tricyclohexyl tin hydroxide (Plictran®)

Nematicides

S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid, 0-ethyl-0'-[4-(methylthio)-m-tolyl]diester (Nemacur")

Insecticides 3-hydroxy-N-methylcrotonamide (dimethylphosphate)ester (Azodrin®)
methylcarbamic acid, ester with 2,3-dihydro-2,2-dimethyl-7-benzofuranol (Furadan®)
0-[2,4,5-trichloro-α-(chloromethyl)benzyl]phosphoric acid, 0',0'-dimethyl ester (Gardona®)
2-mercaptosuccinic acid, diethyl ester, S-ester with thionophosphoric acid, dimethyl ester (Malathion®)
phosphorothioic acid, 0,0-dimethyl, 0-p-nitrophenyl ester (methyl parathion)
methylcarbamic acid, ester with α-naphthol (Sevin®)
methyl 0-(methylcarbamoyl)thiolacetohydroxamate(methomyl)
N'-(4-chloro-o-tolyl)-N,N-dimethylformamidine (Galecron®)
0,0-diethyl-0-(2-isopropyl-4-methyl-6-pyrimidinyl-phosphorothioate (Diazinon®)

The following examples illustrate the insecticidal activity of the compounds of this invention.

EXAMPLE 13

2,3,7-Trichloro-6-quinoxalinesulfonyl fluoride is dissolved in acetone at 10,000 ppm. This formulation is lightly sprayed on adult arthropods. One hundred percent control is achieved on two-spotted mite, boll weevil, and housefly in 72 hours.

EXAMPLE 14

2,3,7-Trichloro-6-quinoxalinesulfonyl fluoride is dissolved in acetone at 500 ppm. This formulation is sprayed directly on beet armyworm eggs. One hundred percent of the treated eggs fail to hatch in three days.

What is claimed is:

1. A compound having the formula

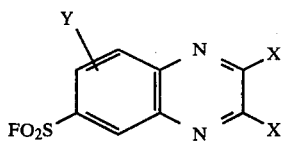

I wherein
X is F or Cl;
Y is Cl, Br, $CH_3O$, $NO_2$ or $CH_3$.

2. A compound of claim 1 wherein X is Cl.

3. A compound of claim 1 wherein Y is a 7-substituent.

4. A compound of claim 1 wherein Y is Cl or $CH_3$.

5. A compound of claim 2 wherein Y is a 7-substituent.

6. A compound of claim 5 wherein Y is Cl or $CH_3$.

7. A compound of claim 1 which is 2,3,7-trichloro-6-quinoxalinesulfonyl fluoride.

8. A fungicidal composition comprising a fungicidally effective amount of a compound of claim 1 and at least one of (a) a surfactant and (b) a suitable diluent.

9. A fungicidal composition comprising a fungicidally effective amount of a compound of claim 2 and at least one of (a) a surfactant and (b) a suitable diluent.

10. A fungicidal composition comprising a fungicidally effective amount of a compound of claim 3 and at least one of (a) a surfactant and (b) a suitable diluent.

11. A fungicidal composition comprising a fungicidally effective amount of a compound of claim 4 and at least one of (a) a surfactant and (b) a suitable diluent.

12. A fungicidal composition comprising a fungicidally effective amount of a compound of claim 5 and at least one of (a) a surfactant and (b) a suitable diluent.

13. A fungicidal composition comprising a fungicidally effective amount of a compound of claim 6 and at least one of (a) a surfactant and (b) a suitable diluent.

14. A fungicidal composition comprising a fungicidally effective amount of the compound of claim 7 and at least one of (a) a surfactant and (b) a suitable diluent.

15. An insecticidal composition comprising an insecticidally effective amount of a compound of claim 1 and at least one of (a) a surfactant and (b) a suitable diluent.

16. An insecticidal composition comprising an insecticidally effective amount of a compound of claim 2 and at least one of (a) a surfactant and (b) a suitable diluent.

17. An insecticidal composition comprising an insecticidally effective amount of a compound of claim 3 and at least one of (a) a surfactant and (b) a suitable diluent.

18. An insecticidal composition comprising an insecticidally effective amount of a compound of claim 4 and at least one of (a) a surfactant and (b) a suitable diluent.

19. An insecticidal composition comprising an insecticidally effective amount of a compound of claim 5 and at least one of (a) a surfactant and (b) a suitable diluent.

20. An insecticidal composition comprising an insecticidally effective amount of a compound of claim 6 and at least one of (a) a surfactant and (b) a suitable diluent.

21. An insecticidal composition comprising an insecticidally effective amount of the compound of claim 7 and at least one of (a) a surfactant and (b) a suitable diluent.

* * * * *